United States Patent
Weidner et al.

(10) Patent No.: US 7,351,741 B2
(45) Date of Patent: Apr. 1, 2008

(54) COMPOUNDS AND COMPOSITIONS FOR DELIVERING ACTIVE AGENTS

(75) Inventors: John J. Weidner, Wappingers Falls, NY (US); Bruce F. Variano, White Plains, NY (US); Shingai Majuru, Brewster, NY (US); Satej Bhandarkar, Garnerville, NY (US); William E. Bay, Ridgefield, CT (US); Lynn Sheilds, Port Chester, NY (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 0 days.

(21) Appl. No.: 10/312,703

(22) PCT Filed: Jun. 29, 2001

(86) PCT No.: PCT/US01/21073

§ 371 (c)(1),
(2), (4) Date: Jun. 25, 2003

(87) PCT Pub. No.: WO02/02509

PCT Pub. Date: Jan. 10, 2002

(65) Prior Publication Data

US 2004/0048777 A1    Mar. 11, 2004

Related U.S. Application Data

(60) Provisional application No. 60/214,893, filed on Jun. 29, 2000.

(51) Int. Cl.
*A61K 31/19* (2006.01)
*A61K 38/00* (2006.01)
*A61K 31/715* (2006.01)
*C07C 229/00* (2006.01)

(52) U.S. Cl. ............... 514/557; 514/2; 514/54; 562/450; 562/455

(58) Field of Classification Search ........... 562/455, 562/450; 514/2, 54, 557
See application file for complete search history.

(56) References Cited

U.S. PATENT DOCUMENTS

| | | | |
|---|---|---|---|
| 3,489,793 A | 1/1970 | Bertelli et al. | |
| 3,931,153 A | 1/1976 | Schmidt et al. | |
| 4,238,506 A | 12/1980 | Stach et al. | |
| 4,442,090 A | 4/1984 | Kakeya et al. | |
| 4,462,991 A | 7/1984 | Higuchi et al. | |
| 4,610,983 A | 9/1986 | Takagawa et al. | 514/230 |
| 4,613,618 A | 9/1986 | Choay et al. | |
| 4,757,066 A | 7/1988 | Shiokari et al. | |
| 4,835,312 A | 5/1989 | Itoh et al. | |
| 4,873,087 A | 10/1989 | Morishito et al. | |
| 4,900,730 A | 2/1990 | Miyauchi | |
| 4,927,928 A | 5/1990 | Shroot et al. | |
| 5,066,487 A | 11/1991 | Morelle et al. | |
| 5,401,516 A | 3/1995 | Milstein et al. | 424/491 |
| 5,443,841 A | 8/1995 | Milstein et al. | 424/491 |
| 5,447,728 A | 9/1995 | Milstein et al. | |
| 5,451,410 A | 9/1995 | Milstein et al. | |
| 5,541,155 A | 7/1996 | Leone-Bay et al. | |
| 5,583,020 A | 12/1996 | Sullivan | |
| 5,629,020 A | 5/1997 | Leone-Bay et al. | |
| 5,643,957 A | 7/1997 | Leone-Bay et al. | |
| 5,650,386 A | 7/1997 | Leone-Bay et al. | |
| 5,705,529 A | 1/1998 | Matyus et al. | |
| 5,709,861 A | 1/1998 | Santiago et al. | |
| 5,714,167 A | 2/1998 | Milstein et al. | |
| 5,766,633 A | 6/1998 | Milstein et al. | |
| 5,773,647 A | 6/1998 | Leone-Bay et al. | |
| RE35,862 E | 7/1998 | Steiner et al. | 424/455 |
| 5,776,888 A | 7/1998 | Leone-Bay et al. | |
| 5,804,688 A | 9/1998 | Leone-Bay et al. | |
| 5,811,127 A | 9/1998 | Milstein et al. | |
| 5,863,944 A | 1/1999 | Leone-Bay et al. | |
| 5,866,536 A | 2/1999 | Leone-Bay et al. | |
| 5,876,710 A | 3/1999 | Leone-Bay et al. | |
| 5,879,681 A | 3/1999 | Leone-Bay et al. | |
| 5,935,610 A | 8/1999 | Leone-Bay et al. | |
| 5,939,381 A | 8/1999 | Leone-Bay et al. | |
| 5,955,503 A | 9/1999 | Leone-Bay et al. | |
| 5,958,457 A | 9/1999 | Santiago et al. | |
| 5,962,710 A | 10/1999 | Gschneidner et al. | |
| 5,965,112 A | 10/1999 | Leone-Bay et al. | |
| 5,989,539 A | 11/1999 | Leone-Bay et al. | |
| 5,990,166 A | 11/1999 | Leone-Bay et al. | |
| 6,001,347 A | 12/1999 | Leone-Bay et al. | |
| 6,051,561 A | 4/2000 | Leone-Bay et al. | |
| 6,060,513 A | 5/2000 | Leone-Bay et al. | |
| 6,071,510 A | 6/2000 | Leone-Bay et al. | |
| 6,071,538 A | 6/2000 | Milstein et al. | |
| 6,084,112 A | 7/2000 | Ho et al. | |
| 6,090,958 A | 7/2000 | Leone-Bay et al. | |
| 6,099,856 A | 8/2000 | Leon-Bay et al. | |
| 6,100,298 A | 8/2000 | Leone-Bay et al. | |
| 6,180,140 B1 | 1/2001 | Leone-Bay et al. | |
| 6,221,367 B1 | 4/2001 | Milstein et al. | |
| 6,242,495 B1 | 6/2001 | Leone-Bay et al. | |

(Continued)

FOREIGN PATENT DOCUMENTS

EP    0036145    9/1981

(Continued)

OTHER PUBLICATIONS

Leone-Bay et al , 4-(4-((2-hydrooxybenzoyl)amino)phenyl)butyric acid as a novel orla delivery agent for rhGH, 1996, vol. 39, p. 2571-2578.*

(Continued)

*Primary Examiner*—Taylor Victor Oh
(74) *Attorney, Agent, or Firm*—Darby & Darby

(57) ABSTRACT

Compounds and compositions for the delivery of active agents are provided. Methods of administration and preparation are provide as well.

27 Claims, No Drawings

U.S. PATENT DOCUMENTS

| | | |
|---|---|---|
| 6,245,359 B1 | 6/2001 | Milstein et al. |
| 6,313,088 B1 | 11/2001 | Leone-Bay et al. |
| 6,344,213 B1 | 2/2002 | Leone-Bay et al. |
| 6,346,242 B1 | 2/2002 | Leone-Bay et al. |
| 6,348,207 B1 | 2/2002 | Milstein et al. |
| 6,358,504 B1 | 3/2002 | Leone-Bay et al. |
| 6,384,278 B1 | 5/2002 | Tang et al. |
| 6,391,303 B1 | 5/2002 | Haas et al. |
| 6,399,798 B2 | 6/2002 | Gschneidner et al. |
| 6,428,780 B2 | 8/2002 | Leone-Bay et al. |
| 6,440,929 B1 | 8/2002 | Milstein et al. |
| 6,461,643 B2 | 10/2002 | Milstein et al. |
| 6,525,020 B2 | 2/2003 | Leone-Bay et al. |
| 6,610,329 B2 | 8/2003 | Santiago et al. |
| 6,623,731 B2 | 9/2003 | Leone-Bay et al. |
| 6,627,228 B1 | 9/2003 | Milstein et al. |
| 6,642,411 B1 | 11/2003 | Leone-Bay et al. |
| 6,646,162 B2 | 11/2003 | Tang et al. |
| 6,663,887 B2 | 12/2003 | Leone-Bay et al. |
| 6,693,073 B2 | 2/2004 | Milstein et al. |
| 6,693,208 B2 | 2/2004 | Gscheidner et al. |
| 6,699,467 B2 | 3/2004 | Leone-Bay et al. |
| 2002/0001591 A1 | 1/2002 | Santiago et al. |
| 2002/0120009 A1 | 8/2002 | Leone-Bay et al. |
| 2004/0023847 A1 | 2/2004 | Gschneidner |

FOREIGN PATENT DOCUMENTS

| | | | |
|---|---|---|---|
| EP | 0576941 | | 1/1994 |
| ES | 369853 | | 7/1971 |
| FR | 4446 | | 11/1966 |
| GB | 2095994 | | 10/1982 |
| JP | 22239980 | | 9/1990 |
| WO | WO 94/23767 | | 10/1994 |
| WO | WO95/28838 | | 11/1995 |
| WO | WO95/28920 | | 11/1995 |
| WO | WO 96/30036 | * | 3/1996 |
| WO | WO96/12473 | | 5/1996 |
| WO | WO96/12474 | | 5/1996 |
| WO | WO96/12475 | | 5/1996 |
| WO | WO96/21464 | | 7/1996 |
| WO | WO-96/30036 A1 | | 10/1996 |
| WO | WO97/10197 | | 3/1997 |
| WO | WO97/36480 | | 10/1997 |
| WO | WO97/47270 | | 12/1997 |
| WO | WO98/21951 | | 5/1998 |
| WO | WO98/25589 | | 6/1998 |
| WO | WO98/34632 | | 8/1998 |
| WO | WO-98/34632 A1 | | 8/1998 |
| WO | WO98/50341 | | 11/1998 |
| WO | WO99/16427 | | 4/1999 |
| WO | WO99/29705 | | 6/1999 |
| WO | WO00/06184 | | 2/2000 |
| WO | WO00/06534 | | 2/2000 |
| WO | WO00/07979 | * | 2/2000 |
| WO | WO00/40203 | | 7/2000 |
| WO | WO00/46182 | | 8/2000 |
| WO | WO00/50386 | | 8/2000 |
| WO | WO00/59480 | | 10/2000 |
| WO | WO00/59863 | | 10/2000 |
| WO | WO01/32130 | | 5/2001 |
| WO | WO01/32596 | | 5/2001 |
| WO | WO01/44199 | | 6/2001 |
| WO | WO01/51454 | | 7/2001 |
| WO | WO01/70219 | | 9/2001 |
| WO | WO01/92206 | | 12/2001 |
| WO | WO02/19969 | | 3/2002 |
| WO | WO02/069937 | | 9/2002 |
| WO | WO02/070438 | | 9/2002 |
| WO | WO02/100338 | | 12/2002 |
| WO | WO03/026582 | | 4/2003 |
| WO | WO03/045306 | | 6/2003 |
| WO | WO03/057170 | | 7/2003 |
| WO | WO03/057650 | | 7/2003 |
| WO | WO 03/057650 | | 7/2003 |

OTHER PUBLICATIONS

Grant et al, Chemical Dictionary 5th ed. , p. 314, 1990.*
Leone-Bay et al, A STN search copy (US 5776888) :1998, p. 2.*
Leone-Bay et al , a STN search copy (US 5773647):1998, p. 2.*
Leon-Bay et al, Synthesis and Evaluation of compounds that Facilitate the Gastrointestinal Absorption of Heparin, 1998, 41, 1163-1171.*
Grant et al , Chemical Dictionary , 1990, p. 305-306, and 313.*
Leone-Bay, A. "N-Acylated alpha-amino acids as novel oral delivery agents for proteins"; Journal of Medicinal Chemistry vol 38, 4263-4269 (1995).
Leone-Bay, A. "Microsphere Formation in a Series of Derivatized Alpha-Amino Acids: Properties, Molecular Modeling, and Oral Delivery of Salmon Calcitonin"; Journal of Medicinal Chemistry vol. 38, 4257-4262 (1995).
Ho Koc-Kan; et al. "A Practical Synthesis of ω-aminoalkanoic acid derivatives form Cycloalkanones" Synthetic Recombinant Human Growth Hormone" Medi 006, Presented at the American Chemical Society, (Mar. 1996) New Orleans, LA.
Leone-Bay, A. "4-[4-[(2-Hydroxybenzoyl)amino]phenyl]butyric acid as a novel oral delivery agent for recombinant human growth hormone"; Journal of Medicinal Chemistry vol. 39, 2571-2578 (1996).
Leone-Bay, A. et al. "The evolution of an oral heparin dosing solution" Drugs of the Future vol. 22(8) 885-891 (1997).
Ho Koc-Kan; et al. "Solution Phase Prepartion of Highly Pure Amide Mixtures Via In-Situ Chlorotrimethylsilane Protection and Activation" Synthetic Communication, vol. 27, No. 5: 883-895 (1997).
Leone-Bay, A. "Acylated non-alpha-amino acids as novel agents for the oral delivery of heparin sodium, USP" Journal of Controlled Release 50: 41-49 (1998).
Leone-Bay, A. "Synthesis And Evaluation Of Compounds That Facilitate The Gastrointestinal Absorption Of Heparin"; Journal of Medicinal Chemistry vol. 41, 1163-1171 (1998).
Francia Farmaceutica "γ-(o-Hydroxybenzamido)-Butyric Acid" Chem Abstracts vol. 10 114838e (1969).
Picciola G.: "Sintesi Di Acidi Chinazolinonici E Benzossazinonici E Studio Delle Loro Proprieta Antiinfiammatorie" IT, Il Farmaco, Ed. Sc. vol. 31, No. 9 pp. 655-664 (1976).
Picciola G.: "Synthesis Of Quniazolinone And Benzoxazainone Acids And Study Of Their Anti-Inflammatory Properties" Chem Abstract 86:5402t (1977).
Johansen, Marianne, et al. "Pro-Drugs As Drug Delivery Systems XIII. Kinetics Of Decompositions. Of N-Mannich Bases Of Salicylamide And Assessment Of Their Suitability As Possible Prodrugs For Amines" Int. J. Pharm. (1980), 7(2): 119-27 (1980).
Brown, G. and Foubister, A.J. "Receptor Binding Sites Of Hypoglycemic Sulfonylureas And Related[(Acylamino)Alkyl]Bezoic Acids" J Med Chem 27, 79-81 (1984).
Amino Yusuke et al. "Phenylalanine Derivatives Enhancing Intestinal Absorption of Insulin in Mice" Chem Pharm Bull 36 pp. 4426-4434 (1988).
Palagiano, F., et al. "Synthesis, Stability And Anticonvulsant Activity Of Two New GABA Prodrugs" Pharmazie 52(4): 272-276 (1997).
U.S. Appl. No. 10/501,205, filed Jul. 9, 2004, Emisphere Technologies, Inc.
O'Shaughnessy, Catherine, et al. "Acylated Non-Alpha-Amino Acids Increase the Permeation of Recombinant Human Growth Hormone Through CACO-2 Monolayers", Abstract 1997 AAPS Annual Meeting Abstracts, Nov. 1997.
O'Shaughnessy, Catherine. "Acylated Non-Alpha-Amino Acids Increase the Permeation of Recombinant Human Growth Hormone Through CACO-2 Monolayers". Poster Presentation at 1997 AAPS Annual Meeting. Nov. 1997.

O'Shaughnessy, Catherine, et al. "Acylated Non-Alpha-Amino Acids Increase the Permeation of Horseradish Peroxidase Through CACO-2 Monolayers", Abstract 1997 AAPS Annual Meting Abstracts. Nov. 1998.

Freeman, John, et al., "The Use of Parallel Synthesis to Prepare Compounds For An In Vivo Assay". Poster Presentation at 217th American Chemical Society Meeting, Mar. 21, 1999.

Freeman, John, et al., "The Use of Parallel Synthesis to Prepare Compounds For An In Vivo Assay". Abstract. American Chemical Society, Mar. 21, 1999.

O'Toole, Doris, et al., Increased Throughput in an In Vivo Assay by Use of Parallel Synthesis Array. Abstract 1998 AAPS Annual Meeting Abstracts. Nov. 1998.

O'Toole, Doris, et al., Increased Throughput in an In Vivo Assay by Use of Parallel Synthesis Array. Poster Presentation at 1998 AAPS Annual Meeting, Anaheim, California. Nov. 16, 1998.

Leone-Bay, Andrea, et al. Oral Delivery of Biologically Active Parathyroid Hormone. Pharmaceutical Research. vol. 18(7):964-970. 2001.

U.S. Appl. No. 09/762,067, filed Aug. 3, 2001, Emisphere Technologies, Inc.

U.S. Appl. No. 11/173,075, filed Jun. 30, 2005, Emisphere Technologies, Inc.

Miltein, S. "Oral Bioavailability of Partially Folded Proteins"; Proceedings of the 1995 Miami Bio/Technology Winter Symposium. Advances in Gene Technology: Protein Engineering and Structural Biology. Short Reports, vol. 6, 13 (Feb. 4-9, 1995).

Ibrahim, El S.A. "Synthesis of 4-Substituted Aminobenzoate Quatemary Salts as Potent Antispasmodic Agents"; Journal of Pharmaceutical Sciences vol. 68(3), 332-335 (Mar. 1979).

Jorgensen, E.C. "Angiotensin II Analogs. IV. Synthesis and Biological Evaluation of Simplified Angiotensins", Journal of Medicinal Chemistry, vol. 13(4) 744-745 (1970).

Declaration Under 37 C.F.R. §1.132 of Halina Levchik, Ph.D., with Exhibits A-I, Jun. 8, 2006.

\* cited by examiner

COMPOUNDS AND COMPOSITIONS FOR DELIVERING ACTIVE AGENTS

FIELD OF THE INVENTION

The present invention relates to compounds for delivering active agents, such as biologically or chemically active agents, to a target. These compounds are well suited for forming non-covalent mixtures with active agents for oral, intracolonic, pulmonary, or other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, proteinoid microspheres have been used to deliver pharmaceuticals. For example, see U.S. Pat. No. 5,401,516, U.S. Pat. No. 5,443,841 and U.S. Pat. No. RE35,862. In addition, certain modified amino acids have been used to deliver pharmaceuticals. See, e.g., U.S. Pat. No. 5,629,020; U.S. Pat. No. 5,643,957; U.S. Pat. No. 5,766,633; U.S. Pat. No. 5,776,888; and U.S. Pat. No. 5,866,536.

However, there is still a need for simple, inexpensive delivery systems which are easily prepared and which can deliver a broad range of active agents by various routes.

SUMMARY OF THE INVENTION

Compounds and compositions that are useful in the delivery of active agents are provided. The present invention encompasses compounds having the following formula, or salts thereof, or mixtures thereof.

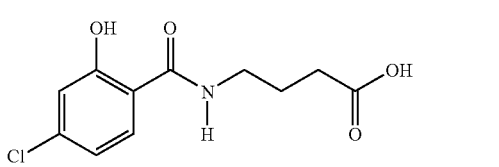

Compound 1

The compositions of the present invention comprise at least one active agent, preferably a biologically or chemically active agent, and at least one of the compounds, or salts thereof, of the present invention. Methods for the preparation and administration of such compositions are also provided.

Also provided are dosage unit forms comprising the compositions. The dosage unit form may be in the form of a solid (such as a tablet, capsule or particle such as a powder or sachet) or a liquid.

Methods for administering a biologically active agent to an animal in need of the agent, especially by the oral, intracolonic or pulmonary routes, with the compositions of the present invention, are also provided, as well as methods of treatment using such compositions. A method of treating a disease in an animal comprising administering a composition of the present invention to the animal in need thereof is provided.

DETAILED DESCRIPTION OF THE INVENTION

Compounds

The compounds may be in the form of the carboxylic acid and/or their salts. Salts include but are not limited to organic and inorganic salts, for example alkali-metal salts, such as sodium, potassium and lithium; alkaline-earth metal salts, such as magnesium, calcium or barium; ammonium salts; basic amino acids such as lysine or arginine; and organic amines, such as dimethylamine or pyridine. Preferably, the salts are sodium salts. The salts may be mono- or multivalent salts, such as monosodium salts and di-sodium salts. The salts may also be solvates including ethanol solvates.

In addition, poly amino acids and peptides comprising one or more of these compound may be used.

An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids. One or more of the amino acids or peptide units may be acylated or sulfonated.

The compounds described herein may be derived from amino acids and can be readily prepared from amino acids by methods within the skill of those in the art based upon the present disclosure and the methods described in WO96/30036, WO97/36480, U.S. Pat. No. 5,643,957 and U.S. Pat. No. 5,650,386. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, N.Y. (1981), the disclosure of which is hereby incorporated herein by reference.

Salts of the present compound may be made by methods known in the art. For example, sodium salts may be made by dissolving the compound in ethanol and adding aqueous sodium hydroxide.

The compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

According to one embodiment, the compound is employed in its anhydrous form.

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of muco-polysaccharides; carbohydrates; lipids; other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone-releasing hormones; interferons, including $\alpha$, $\beta$ and $\gamma$; interleukin-1; interleukin-2; insulin, including porcine, bovine, human, and human recombinant, optionally having counter ions including sodium, zinc, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; vitamins; analogs, fragments, mimetics or polyethylene glycol (PEG)-modified derivatives of these compounds; or any combination thereof. Other suitable forms of insulin, including, but not limited to, synthetic forms of insulin, are described in U.S. Pat. Nos. 4,421,685, 5,474,978, and 5,534,488, each of which is hereby incorporated by reference in its entirety.

Delivery Systems

The compositions of the present invention comprise a delivery agent and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration.

The administration compositions may be in the form of a liquid. The dosing vehicle may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycols, sorbitol, maltitol, and sucrose. Dosing solutions may be prepared by mixing a solution of the delivery agent compound with a solution of the active agent, just prior to administration. Alternately, a solution of the delivery agent (or active agent) may be mixed with the solid form of the active agent (or delivery agent). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze drying, precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions may deliver active agents more efficiently than prior compositions, lower amounts of biologically or chemically active agents than those used in prior dosage unit forms or delivery systems can be administered to the subject, while still achieving the same blood levels and/or therapeutic effects.

The presently disclosed compounds deliver biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

EXAMPLE 1

Compound Preparation

1a. Preparation of Compound 1.

4-Chlorosalicylic acid (10.0 g, 0.0579 mol) was added to a one-neck 250 ml round-bottomed flask containing about 50 ml methylene chloride. Stirring was begun and continued for the remainder of the reaction. Coupling agent 1,1-carbonyldiimidazole (9.39 g, 0.0579 mol) was added as a solid in portions to the flask. The reaction was stirred at room temperature for approximately 20 minutes after all of the coupling agent had been added and then ethyl-4-aminobutyrate hydrochloride (9.7 g, 0.0579 mol) was added to the flask with stirring. Triethylamine (10.49 ml, 0.0752 mol) was added dropwise from an addition funnel. The addition funnel was rinsed with methylene chloride. The reaction was allowed to stir at room temperature overnight.

The reaction was poured into a separatory funnel and washed with 2N HCl and an emulsion formed. The emulsion was left standing for two days. The emulsion was then filtered through celite in a fritted glass funnel. The filtrate was put back in a separatory funnel to separate the layers. The organic layer was dried over sodium sulfate, which was then filtered off and the filtrate concentrated by rotary evaporation. The resulting solid material was hydrolyzed with 2N NaOH, stored overnight under refrigeration, and then hydrolyzing resumed. The solution was acidified with 2N HCl and the solids that formed were isolated, dried under vacuum, and recrystallized twice using methanol/water. Solids precipitated out overnight and were isolated and dried. The solids were dissolved in 2N NaOH and the pH of the sample was brought to pH 5 with 2N HCl. The solids were collected and HPLC revealed a single peak. These solids were then recrystallized in methanol/water, isolated, and then dried under vacuum, yielding 4.96 g (33.0%) of 4-(4 chloro-2-hydroxybenzoyl)aminobutyric acid. ($C_{11}H_{12}ClNO_4$; Molecular weight 257.67.) Melting point: 131-133° C. Combustion analysis: % C: 51.27(calc.), 51.27 (found); % H: 4.69 (calc.), 4.55 (found); % N: 5.44 (calc.), 5.30 (found). H NMR Analysis: ($d_6$-DMSO): δ 13.0, s, 1H (COOH); δ 12.1, s, 1H (OH); δ 8.9, t, 1H (NH); δ 7.86, d, 1H (H ortho to amide); δ 6.98, d, 1H (H ortho to phenol OH); δ 6.96, d, 1H, (H meta to amide); δ 3.33, m, 2H ($CH_2$ adjacent to NH); δ 2.28, t, 2H ($CH_2$ adjacent to COOH); 67 1.80, m, 2H (aliphatic $CH_2$ beta to NH and $CH_2$ beta to COOH)

1b. Additional Preparation of Compound 1.

4-Chlorosalicylic acid (25.0 g, 0.1448 mol) was added to a one-neck 250 ml round-bottomed flask containing about 75-100 ml methylene chloride. Stirring was begun and continued to the remainder of the reaction. Coupling agent 1,1-carbonyldiimidazole (23.5 g, 0.1448 mol) was added as a solid in portions to the flask. The reaction was stirred at room temperature for approximately 20 minutes after all of the coupling agent had been added and then ethyl-4-aminobutyrate hydrochloride (24.3 g 0.1448 mol) was added to the flask with stirring. Triethylamine (26.0 ml, 0.18824 mol) was added dropwise from an addition funnel. The addition funnel was rinsed with methylene chloride. The reaction was allowed to stir at room temperature overnight.

The reaction was poured into a separatory funnel and washed with 2N HCl and an emulsion formed. The emulsion was filtered through celite in a fritted glass funnel. The filtrate was put back in a separatory funnel to separate the layers. The organic layer was washed with water and brine, then dried over sodium sulfate, which was then filtered off and the filtrate concentrated by rotary evaporation. The resulting solid material was hydrolyzed with 2N NaOH overnight. The solution was acidified with 2N HCl and the brown solids that formed were recrystallized using methanol/water, hot filtering off insoluble black material. White solids precipitated out and were isolated and dried, yielding 11.68 g (37.0%)of 4-(4 chloro-2-hydroxybenzoyl)aminobutyric acid. ($C_{11}H_{12}ClNO_4$; Molecular weight 257.67.) Melting point: 129-133° C. Combustion analysis: % C: 51.27 (calc.), 51.26 (found); % H: 4.69 (calc.), 4.75 (found); % N: 5.44 (calc.), 5.32 (found). H NMR Analysis: ($d_6$-DMSO): δ 13.0, s, 1H (COOH); δ 12.1, s, 1H (OH); δ 8.9, t, 1H (NH); δ 7.86, d, 1H (H ortho to amide); 67 6.98, d, 1H (H ortho to phenol OH); δ 6.96, d, 1H, (H meta to amide); δ 3.33, m, 2H ($CH_2$ adjacent to NH); δ 2.28, t, 2H ($CH_2$ adjacent to COOH); δ 1.80, m, 2H (aliphatic $CH_2$ beta to NH and $CH_2$ beta to COOH).

1c. Additional Preparation of Compound 1

(4-[(4-Chloro-2-hydroxybenzoyl)amino]butanoic acid)

A 22 L, five neck, round bottom flask was equipped with an overhead stirrer, 1 L Dean-Stark trap with reflux condenser, thermocouple temperature read out, and heating mantle. The following reaction was run under a dry nitrogen atmosphere. Reagent n-butanol (5000 mL) and 4-chlorosalicylic acid (2000 g, 11.59 mol) were charged to the reaction flask. The Dean-Stark trap was filled with n-butanol (1000 mL). Concentrated sulfuric acid (50 g) was added. The reaction mixture was heated to reflux for approximately 120 hours. Approximately 206 mL water was collected in the trap during this time. The heating mantle was removed and the reaction mixture allowed to cool to ambient temperature. The Dean-Stark trap was drained and removed. Deionized water (1000 mL) was charged. The biphasic mixture was stirred for 10 minutes. Stirring was stopped and the phases allowed to separate. The lower aqueous phase was siphoned off and discarded. A 10 wt % aqueous solution of sodium bicarbonate (1000 mL) was charged to the reaction mixture. The mixture was stirred for 10 minutes. The reaction mixture was tested with pH paper to ensure the pH of the solution was greater than 7. Water (500 mL) was added to the reaction mixture. The stirring was stopped and the phases allowed to separate. The lower aqueous layer was siphoned off and discarded. The reaction mixture was washed with another 500 mL portion of deionized water. The reactor was set up for atmospheric distillation into a tared 5 L receiver. The mixture was distilled until the pot temperature rose to between 140 and 150° C. The distillation was switched from atmospheric distillation to vacuum distillation. The pressure in the distillation setup was slowly lowered to 100 mmHg. The pot temperature fell and the remaining n-butanol and n-butyl ether (a reaction byproduct) distilled off. The heating was stopped and the reaction mixture allowed to cool to ambient temperature. The vacuum was broken with dry nitrogen. The crude butyl ester was transferred to a 5 L pot flask of a vacuum distillation setup. The crude butyl ester was distilled at a pressure between 0.2 and 0.5 mmHg. The forerun collected at a head temperature of <40° C. was discarded. The butyl 4-chloro-2-hydroxybenzoate fraction was collected at a head temperature between 104 and 112° C. This fraction had a weight of 2559 g. The yield was 96%.

A 22 L, five neck, round bottom flask was equipped with an overhead stirrer, reflux condenser, thermocouple temperature read out, and a heating mantle. The reactor was purged with nitrogen. Butyl 4-chloro-2-hydroxybenzoate (2559 g, 11.2 moles) and reagent methanol (10,000 mL) were charged to the reaction flask, and the contents were stirred until a solution was obtained. The reaction mixture was filtered through a Buchner funnel and returned to the reactor. The stirring rate was increased, and gaseous ammonia was added rapidly to the headspace of the reactor. The ammonia gas addition was continued until the temperature of the reactor reached 45° C. The addition of the ammonia was suspended and the agitation rate lowered. The reaction was allowed to cool to ambient temperature. Ammonia gas addition, as described above, was repeated until the reaction was complete as indicated by liquid chromatography. Seven ammonia charges over five days were needed to complete the reaction. Approximately half of the solvent was removed by atmospheric distillation. The reaction mixture was cooled to ambient temperature and 5 L of deionized water was added. Concentrated hydrochloric acid (approximately 500 mL) was added slowly to the reactor until the pH of the reaction mixture was between 4 and 5. The resulting precipitate was collected by vacuum filtration through a large sintered glass funnel. The product filter cake was washed with 2000 mL of deionized water, and dried at 50° C. for 32 hours to give 1797 g of 4-chloro-2-hydroxybenzamide. The yield was 94%.

A 22 L, five neck, round bottom flask was equipped with an overhead stirrer, reflux condenser, addition funnel, thermocouple temperature read out, and a heating mantle. The reactor was purged with nitrogen. Acetonitrile (4700 mL) and 4-chloro-2-hydroxybenzamide (1782 g, 10.4 mol) were charged to the reaction flask and the stirring was started. Pyridine (1133 mL, 14.0 mol) was charged to the reactor. The resulting reaction slurry was cooled to less than 10° C. with an ice bath. Ethyl chloroformate (1091 mL, 1237 g, 11.4 mol) was placed in the addition funnel and charged slowly to the stirred reaction mixture such that the temperature of the reaction mixture did not exceed 15° C. during the addition. The temperature of the reaction mixture was held between 10 and 15° C. for 30 minutes after the ethyl chloroformate addition was complete. The ice bath was removed, and the reaction mixture was warmed to ambient temperature. The reaction mixture was then slowly heated to reflux and held at that temperature for 18 hours. Liquid chromatographic analysis of the reaction mixture indicated that the reaction was only 80% complete. Approximately half of the solvent was removed by atmospheric distillation. The reaction mixture was cooled first to ambient temperature and then to <10° C. with an ice bath. Additional pyridine (215 mL, 2.65 mol) was added to the reaction mixture. Ethyl chloroformate (235 g, 2.17 mol) was added slowly via an addition funnel to the cold reaction mixture. The reaction mixture was held between 10 and 15° C. for 30 minutes after the ethyl chloroformate addition was complete. The ice bath was removed, and the reaction mixture was warmed to ambient temperature. The reaction mixture was then slowly heated to reflux and held at that temperature for 18 hours, after which time liquid chromatographic analysis indicated that the reaction was complete. The reaction mixture was cooled first to ambient temperature and then to <10° C. with an ice bath. Water (1600 mL) was added slowly via an addition funnel and the resulting slurry held at <10° C. for 90 minutes. The solid product was collected by vacuum filtration through a large sintered glass funnel. The product filter cake was washed with deionized water and vacuum dried at 50° C. for 18 hours to give 1914 g of 7-chloro-2H-1,3-benzoxazine-2,4(3H)-dione as a tan solid. The yield was 83%.

A 22 L, five neck, round bottom flask was equipped with an overhead stirrer, reflux condenser, thermocouple temperature read out, and heating mantle. The following reaction was run under a dry nitrogen atmosphere. 7-Chloro-2H-1,3-benzoxazine-2,4(3H)-dione (1904 g, 9.64 mol), ethyl 4-bromobutyrate (1313 mL, 9.18 mol), and N,N-dimethylacetamide (4700 mL) were charged under a nitrogen purge. The reaction mixture was heated to 70° C. Sodium carbonate (1119 g, 10.55 mol) was charged to the clear solution in five equal portions over approximately 40 minutes. The reaction mixture was held at 70° C. overnight. The reaction was cooled to 55° C. The inorganic solids were removed by vacuum filtration through a sintered glass funnel. The reaction flask was rinsed with 2B-ethanol (2000 mL) and this rinse used to wash the filter cake. The reaction flask was cleaned with deionized water. The filtrate was returned to the clean reaction flask. The filtrate was cooled in an ice bath. Deionized water (9400 mL) was added slowly with an addition funnel. The chilled mixture was allowed to stir overnight. The resulting solids were recovered by vacuum filtration through a sintered glass funnel. The product cake was washed with deionized water. The ethyl 3-(4-butanoate)-7-chloro-2H-1,3-benzoxazine-2,4-(3H)-dione had a weight of 2476.0 g. The yield was 82.2%.

A 12 L, stainless steel reactor was equipped with an overhead stirrer, reflux condenser, thermocouple temperature read out, addition funnel, and heating mantle. The following reaction was run under a dry nitrogen atmosphere. Water (3 L) and ethyl 3-(4-butanoate)-7-chloro-2H-1,3-benzoxazine-2,4-(3H)-dione (1118 g, 3.58 mol) were charged to the reactor and stirring was started. A solution of sodium hydroxide (574 g, 4.34 mol) in water (2 L) was added slowly to the reaction slurry. The reaction was heated to 70° C. for 6 hours, and then allowed to cool slowly to ambient temperature. The reaction mixture was filtered through a Buchner funnel.

A 22 L five neck round bottom flask was equipped with an overhead stirrer, reflux condenser, thermocouple temperature read out, and an addition funnel. Deionized water (1880 mL) and concentrated hydrochloric acid (1197 g, 12.04 mol) were charged to the reactor. The hydrolysate from above was added slowly via addition funnel to the acid solution. The pH of the resulting slurry was adjusted to 3 by adding additional hydrochloric acid (160 mL, 1.61 mol) The product solids were collected by filtration through a sintered glass funnel and dried in a vacuum oven at 50° C. for 24 hours to give 1109.3 g of 4-[(4-chloro-2-hydroxy-benzoyl)amino]butanoic acid as an off white solid. The yield was quantitative.

EXAMPLE 1d

Preparation of Anhydrous Sodium 4-[(2-Hydroxybenzoyl)amino]butanoate

A 22 L, five neck round bottom flask, was equipped with an overhead stirrer, reflux condenser, thermocouple temperature read out, and heating mantle. The following reaction was run under a dry nitrogen atmosphere. Reagent acetone (13000 mL) and 4-[(4-chloro-2-hydroxy-benzoyl)amino]butanoic acid (500.0 g, 1.94 mol) were charged to the reactor and stirring was started. The reaction slurry was heated to 50° C. until a hazy brown solution was obtained. The warm solution was pumped through a warm pressure filter dressed with Whatman #1 paper into a clean 22 L reactor. The clear yellow filtrate was heated to 50° C. while stirring. Sodium hydroxide solution (50% aqueous; 155 g, 1.94 mol) was charged to the reactor while maintaining vigorous agitation. After the base addition was complete, the reactor was heated to reflux (60° C.) for 2.5 hours and then allowed to cool slowly to ambient temperature. The product was isolated by vacuum filtration through a sintered glass funnel and dried in a vacuum oven at 50° C. for 24 hours to give 527.3 g of sodium 4-[(2-hydroxybenzoyl)amino]butanoate as an off-white solid. The yield was 97.2%.

EXAMPLE 1e

Preparation of Sodium 4-[(4-chloro-2-Hydroxybenzoyl)amino]butanoate

A 22 L flask was equipped with an overhead stirrer. Deionized water (2000 mL) and 4-[(4-chloro-2-hydroxybenzoyl)amino]butanoic acid (380.0 g, 1.47 mol) were added and stirring was started. A solution of sodium hydroxide (59.0 g, 1.48 mol) in water (500 mL) was added to the reactor. Water (1500 mL) was added to the reactor, and the resulting slurry was heated until a complete solution was obtained. The reaction mixture was cooled to ambient temperature, and then concentrated to dryness under reduced pressure. The resulting solids were scraped from the flask and vacuum dried at 50° C. to give 401.2 g of sodium 4-[(2-hydroxybenzoyl)amino]butanoate as an off-white solid. The yield was 96.9%.

EXAMPLE 1f

Preparation of Sodium 4-[(2-Hydroxybenzoyl)-amino]butanoate Through the Isopropanol Solvate A one liter, four neck round bottom flask was equipped with an overhead stirrer, reflux condenser, thermocouple temperature read out, and heating mantle. The following reaction was run under a dry nitrogen atmosphere. Isopropanol (400 mL) and 4-[(4-chloro-2-hydroxy-benzoyl)amino]butanoic acid (25.0 g, 0.09 mol) were charged to the reactor and stirring was started. The reaction slurry was heated to 50° C. until a hazy brown solution was obtained. The warm solution was filtered through a warm pressure filter dressed with Whatman #1 paper into a clean 1 L reactor. The clear yellow filtrate was heated to 62° C. while stirring. Sodium hydroxide solution (50% aqueous; 7.2 g, 0.09 mol) was charged to the reactor while maintaining vigorous agitation. After the base addition was complete, the reactor was heated to reflux (72° C.) and then allowed to cool slowly to ambient temperature. The product was isolated by vacuum filtration through a sintered glass funnel and vacuum dried at 50° C. for 24 hours to give 23.16 g of sodium 4-[(2-hydroxybenzoyl)amino]butanoate as an off-white solid. The yield was 92%.

EXAMPLE 1g

Capsule Preparation

Capsules for primate dosing containing the monosodium salt of compound 1 (as prepared in example 1d) and insulin were prepared as follows. The compound 1 monosodium salt and QA307X zinc insulin crystals human: proinsulin derived (recombinant DNA origin) (available from Eli-Lilly & Co. of Indianapolis, Ind.) were first screened through a 35 mesh Tyler standard sieve and the required amount weighed. Screened compound 1 monosodium salt and insulin were blended using geometric sieving method in a suitably sized glass mortar. The materials in the mortar were mixed well with a glass pestle. A spatula was used for scrapping the sides of the mortar. The resulting formulation was transferred to a plastic weigh boat for capsule filling. The formulation was hand packaged into size #0 Torpac hard gelatin capsules (available from Torpac, Inc. of Fairfield, N.J.). Each capsule fill weight was dependent on the individual animal weight. Capsules doses of compound 1 were 100 mg/kg, 75 mg/kg and 50 mg/kg (as monosodium salt). Capsule doses of insulin were 0.25 to 0.5 mg per kg.

EXAMPLE 2

Insulin—Oral Delivery

A. Rat Studies Oral dosing (PO) compositions of delivery agent compound (prepared as in Example 1a or 1b as indicated below) and zinc human recombinant insulin (available from Calbiochem-Novabiochem Corp., La Jolla, Calif. (Catalog # 407694)) were prepared in deionized water. Typically, 500 mg of delivery agent compound was added to 1.5 ml of water. The free acid of the delivery agent compound was converted to the sodium salt by stirring the resultant solution and adding one equivalent of sodium hydroxide. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted. (For example, for compound 1a, a total of 258.5 ml 10N NaOH was added to 501 mg compound in 1.5 ml water, final pH 7.73.) Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 10N NaOH and 50 ml 1N NaOH) was added to the solution and mixed by inverting. The final delivery agent compound dose, insulin dose and dose volume amounts are listed below in Table 1.

The dosing and sampling protocols were as follows. Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically at time=15, 30, 60, 120 and 180 minutes after administration. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum human insulin concentrations (µU/ml) were measured for each time point for each of the five animals in each dosing group. The five values for each time point were averaged and the results plotted as serum insulin concentration versus time. The maximum (peak) and the area under the curve (AUC) are reported below in Table 1. Previous experiments revealed no measurable levels of human insulin following oral dosing with human insulin alone.

TABLE 1

Insulin-Oral Delivery

| Compound | volume dose (ml/kg) | Compound Dose (mg/kg) | Insulin Dose (mg/kg) | Mean Peak Serum Human Insulin (µU/ml ± SE) | AUC |
|---|---|---|---|---|---|
| 1a | 1.0 | 200 | 0.5 | 1457 ± 268 | 58935 |
| 1b | 1.0 | 200 | 0.5 | 183 ± 89 | 8674 |
| 1b | 1.0 | 200 | 0.5 | 136 ± 52 | 5533 |
| 1b | 1.0 | 200 | 0.5 | 205 ± 61 | 7996 |
| 1b | 1.0 | 200 | 0.5 | 139 ± 43 | 5271 |

B. Monkey Studies

All animal protocols adhered to the "Principles of Laboratory Animal Care" and were Institutional Animal Care and Use Committee (IACUC) approved.

The dosing protocol for administering the capsules to each animal was as follows. Baseline plasma samples were obtained from the animals prior to dosing. Groups of four cynomolgus monkeys, two males and two females, weighing 2-3 kg were fasted for 4 hours prior to dosing and up to 2 hours after dosing. The animals were anesthetized with an intramuscular injection of 10 mg/kg ketamine hydrochloride immediately prior to dosing. Each animal was administered varying doses of compound 1 (25-100 mg/kg) in combination with varying doses of insulin 0.25-0.5 mg/kg insulin as 1 capsule. Water was available throughtout the dosing period and 400 ml of juice was made available to the animal overnight prior to dosing and throughout the dosing period. The animal was restrained in a sling restraint. A capsule was placed into a pill gun, which is a plastic tool with a cocket plunger and split rubber tip to accommodate a capsule. The pill gun was inserted into the espophagus of the animal. The plunger of the pill gun was pressed to push the capsule out of the rubber tip into the espophagus. The pill gun was then retracted. The animals mouth was held closed and approximately 5 ml reverse osmosis water was administered into the mouth from the side to induce a swallowing reflex. The throat of the animal was rubbed further to induce the swallowing reflex.

Citrated blood samples (1 mL each) were collected by venipuncture from an appropriate vein at 1 hour before dosing and at 10, 20, 30, 40, and 50 minutes and 1, 1.5, 2, 3, 4, and 6 hours after dosing. Each harvested plasma sample was divided into two portions. One portion was frozen at −80° C. and shipped to another location for insulin assay. The other portion was used in the blood glucose assay. Four monkeys also received insulin subcutaneously (0.02 mg/kg). Blood samples were collected and analyzed as described above.

Insulin Assays. Serum insulin levels were measured using the Insulin ELISA Test Kit (DSL, Webster, Tex.).

Glucose Assays. Blood glucose measurements were performed using ONETOUCH® Glucose Monitoring System from Live Scan Inc., Newtown, Pa.

The results are shown in Table 1A below.

TABLE 1A

Insulin - Oral Delivery to Monkeys

| Compound | Compound Dose (mg/kg) | Insulin Dose (mg/kg) | Mean Peak Serum Human Insulin (μU/ml ± SE) | Mean Peak Blood Glucose Reduction (μU/ml ± SE) |
|---|---|---|---|---|
| 1d | 100 | 0.5 | 91.4 ± 45 | 52.3 ± 5.3 |
| 1d | 50 | 0.5 | 124.1 ± 51.95 | −61 ± 12.7 |
| 1d | 25 | 0.5 | 87.14 ± 53.85 | −28.75 ± 21.59 |
| 1d | 25 | 0.25 | 36.35 ± 32.3 | −19 ± 10.21 |

EXAMPLE 3

Cromolyn—Oral Delivery

Dosing solutions containing a delivery agent compound (prepared as in Example 1b) and cromolyn, disodium salt (cromolyn) (Sigma, Milwaukee, Wis.) were prepared in deionized water. The free acid of the delivery agent compound was converted to the sodium salt with one equivalent of sodium hydroxide. This mixture was vortexed and placed in a sonicator (about 37° C.). The pH was adjusted to about 7-7.5 with aqueous NaOH. Additional NaOH was added, if necessary, to achieve uniform solubility, and the pH re-adjusted. The mixture was vortexed to produce a uniform solution, also using sonication and heat if necessary. The delivery agent compound solution was mixed with cromolyn from a stock solution (175 mg cromolyn/ml in deionized water, pH adjusted, if necessary, with NaOH or HCl to about 7.0, stock solution stored frozen wrapped in foil, then thawed and heated to about 30° C. before using). The mixture was vortexed to produce a uniform solution, also using sonication and heat if necessary. The pH was adjusted to about 7-7.5 with aqueous NaOH. The solution was then diluted with water to the desired volume (usually 2.0 ml) and concentration and stored wrapped in foil before use. The final delivery agent compound and cromolyn doses, and the dose volumes are listed below in Table 2.

The typical dosing and sampling protocols were as follows. Male Sprague-Dawley rats weighing between 200-250 g were fasted for 24 hours and were anesthetized with ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected via the tail artery, typically at 0.25, 0.5, 1.0 and 1.5 hours after dosing. Serum cromolyn concentrations were measured by HPLC. Samples were prepared as follows: 100 μl serum was combined with 100 μl 3N HCl and 300 μl ethyl acetate in an eppendorf tube. The tube was vortexed for 10 minutes and then centrifuged for 10 minutes at 10,000 rpm. 200 μl ethyl acetate layer was transferred to an eppendorf tube containing 67 μl 0.1 M phosphate buffer. The tube was vortexed for 10 minutes and then centrifuged for 10 minutes at 10,000 rpm. The phosphate buffer layer was then transferred to an HPLC vial and injected into the HPLC (column=Keystone Exsil Amino 150×2 mm i.d., 5 μm, 100 Å (Keystone Scientific Products, Inc.); mobile phase=35% buffer(68 mM $KH_2PO_4$ adjusted to pH 3.0 with 85% $H_3PO_4$)/65% acetonitrile; injection volume=10 μl; flow rate=0.30 ml/minute; cromolyn retention time=5.5 minutes; absorbance detected at 240 nm). Previous studies indicated baseline values of about zero.

Results from the animals in each group were averaged for each time point and the highest of these averages (i.e., mean peak serum cromolyn concentration) is reported below in Table 2.

TABLE 2

Cromolyn - Oral Delivery

| Compound | volume dose (ml/kg) | Compound Dose (mg/kg) | Cromolyn Dose (mg/kg) | Mean Peak serum [cromolyn] ± SD (SE) |
|---|---|---|---|---|
| 1b | 1 | 200 | 25 | 0.70 ± 0.36 (0.16) |

EXAMPLE 4

Recombinant Human Growth Hormone (rhGH)—Oral Delivery

Oral gavage (PO) dosing solutions of delivery agent compound (prepared as in Example 1a or 1b as indicated in Table 3 below) and rhGH were prepared in phosphate buffer. The free acid of the delivery agent compound was converted to the sodium salt with one equivalent of sodium hydroxide. Typically, a solution of the compound was prepared in phosphate buffer and stirred, adding one equivalent of sodium hydroxide (1.0 N) when making the sodium salt. Additional NaOH was added, if necessary, to achieve uniform solubility, and the pH re-adjusted. The final dosing solutions were prepared by mixing the compound solution with an rhGH stock solution (15 mg rhGH/ml made by mixing as powders 15 mg rhGH, 75 mg D-mannitol, 15 mg glycine and 3.39 mg dibasic sodium phosphate, then diluting with 2% glycerol) and diluting to the desired volume (usually 3.0 ml). The compound and rhGH doses and the dose volumes are listed below in Table 3.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically at time=15, 30, 45 and 60 minutes after administration. Serum rHGH concentrations were quantified by an rHGH immunoassay test kit (Kit # K1F4015 from Genzyme Corporation Inc., Cambridge, Mass.). Previous studies indicated baseline values of about zero.

Results from the animals in each group were averaged for each time point. The maximum of these averages (i.e., the mean peak serum rhGH concentration) is reported below in Table 3. (In the cases where no standard deviation (SD) or standard error (SE) is given below, the five samples from each time period were pooled prior to assaying.)

TABLE 3 rhGH - Oral Delivery

| Compound | Volume dose (ml/kg) | Compound Dose (mg/kg) | rhGH Dose (mg/kg) | Mean Peak Serum [rhGH] ± SD (SE) (ng/ml) |
|---|---|---|---|---|
| 1a | 1 | 200 | 3 | 99.35 |
| 1a | 1 | 200 | 3 | 42.62 |
| 1b | 1 | 200 | 3 | 84.01 ± 73.57 (32.90) |
| 1b | 1 | 200 | 3 | 50.44 ± 34.13 (15.26) |

EXAMPLE 5

Interferon—Oral Delivery

Dosing solutions of delivery agent compound (prepared as in Example 1b) and human interferon (IFN) were prepared in deionized water. The free acid of the delivery agent compound was converted to the sodium salt with one equivalent of sodium hydroxide. Typically, a solution of the delivery agent compound was prepared in water and stirred, adding one equivalent of sodium hydroxide (1.0 N) when making the sodium salt. This mixture was vortexed and placed in a sonicator (about 37° C.). The pH was adjusted to about 7.0 to 8.5 with aqueous NaOH. The mixture was vortexed to produce a uniform suspension or solution, also using sonication and heat if necessary. Additional NaOH was added, if necessary, to achieve uniform solubility, and the pH re-adjusted. The delivery agent compound solution was mixed with an IFN stock solution (about 22.0 to 27.5 mg/ml in phosphate buffered saline) and diluted to the desired volume (usually 3.0 ml). The final delivery agent compound and IFN doses, and the dose volumes are listed below in Table 4.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically at time=0, 15, 30, 45, 60 and 90 minutes after administration. Serum IFN concentrations were quantified using Cytoscreen Immunoassay Kit for human IFN-alpha (catalog # KHC4012 from Biosource International, Camarillo, Calif.). Previous studies indicated baseline values of about zero. Results from the animals in each group were averaged for each time point. The maximum of these averages (i.e., the mean peak serum IFN concentration) is reported below in Table 4.

TABLE 4

Interferon - Oral Delivery

| Compound | Volume dose (ml/kg) | Compound Dose (mg/kg) | IFN Dose (mg/kg) | Mean Peak Serum [IFN] (ng/ml) ± SD (SE) |
|---|---|---|---|---|
| 1b | 1.0 | 200 | 1.0 | 17.80 ± 13.52 (6.05) |

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A compound of the formula

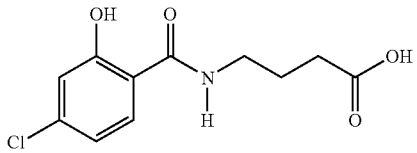

or a salt thereof.

2. A composition comprising:
   (A) at least one active agent; and
   (B) a compound having the formula

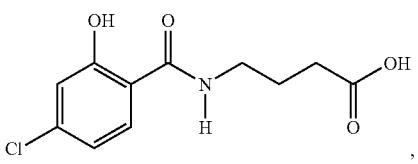

a salt thereof, or a mixture thereof.

3. The composition of claim 2, wherein the active agent is selected from the group consisting of a biologically active agent, a chemically active agent, and a combination thereof.

4. The composition of claim 3, wherein the biologically active agent is at least one protein, polypeptide, peptide, hormone, polysaccharide, mucopolysaccharide, carbohydrate, or lipid.

5. The composition of claim 2, wherein the active agent is selected from the group consisting of:

growth hormones, human growth hormones, recombinant human growth hormones, bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor, insulin-like growth factor-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine, parathyroid hormone, fragments of parathyroid hormone, antimicrobials, anti-fungal agents, vitamins; and any combination thereof.

6. The composition of claim 2, wherein the active agent is insulin, human growth hormone, interferon, cromolyn sodium or combinations thereof.

7. The composition of claim 2, wherein the active agent is insulin.

8. The composition of claim 2, wherein the active agent is interferon.

9. A dosage unit form comprising:
(A) the composition of claim 2; and
(B) (a) an excipient
  (b) a diluent,
  (c) a disintegrant,
  (d) a lubricant,
  (e) a plasticizer,
  (f) a colorant,
  (g) a dosing vehicle, or
  (h) any combination thereof.

10. The dosage unit form of claim 9, wherein the active agent is selected from the group consisting of a biologically active agent, a chemically active agent, and a combination thereof.

11. The dosage unit form of claim 10, wherein the biologically active agent is a protein, polypeptide, peptide, hormone, polysaccharide, mucopolysaccharide, carbohydrate, or lipid.

12. The dosage unit form of claim 9, wherein the active agent is selected from the group consisting of:
growth hormones, human growth hormones, recombinant human growth hormones, bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor, insulin-like growth factor-1, heparin, unfractionated heparin, heparinoids, dermatans, chondroitins, low molecular weight heparin, very low molecular weight heparmn, ultra low molecular weight heparmn, calcitonin, salmon calcitonin, eel calcitonin, human calcitonin; erythropoietin, atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine, parathyroid hormone, fragments of parathyroid hormone, antimicrobials, anti-fungal agents, vitamins; and any combination thereof.

13. The dosage unit form of claim 9, wherein the active agent is insulin, human growth hormone, interferon, cromolyn sodium or combinations thereof.

14. The dosage unit form of claim 9, wherein the active agent is insulin.

15. The dosage unit form of claim 9, wherein the active agent is interferon.

16. The dosage unit form of claim 9, wherein the dosage unit form is in the form of a tablet, a capsule, a particle, a powder, a sachet, or a liquid.

17. The dosage unit form of claim 9, wherein the dosing vehicle is a liquid selected from the group consisting of water, 25% aqueous propylene glycol, phosphate buffer, 1,2-propane diol, ethanol, and any combination thereof.

18. A method for preparing a composition comprising mixing:
(A) at least one active agent;
(B) the compound of claim 1; and
(C) optionally, a dosing vehicle.

19. Anhydrous sodium 4-[(4-chloro-2-hydroxybenzoyl)amino]butanoate.

20. A composition comprising:
(a) at least one active agent; and
(b) the anhydrous compound of claim 19.

21. The composition of claim 20, wherein the active agent is insulin.

22. A solid oral dosage form comprising:
(A) the composition of claim 21; and
(B) (a) an excipient,
  (b) a diluent,
  (c) a disintegrant,
  (d) a lubricant,
  (e) a plasticizer,
  (f) a colorant,
  (g) a dosing vehicle, or
  (h) any combination thereof.

23. Sodium 4-[(4-chloro-2-hydroxybenzoyl)amino]butanoate isopropanol solvate.

24. A composition comprising:
(a) at least one active agent; and
(b) the compound of claim 23.

25. The composition of claim 24, wherein the active agent is insulin.

26. A solid oral dosage form comprising:
(A) the composition of claim 25; and
(B) (a) an excipient,
  (b) a diluent,
  (c) a disintegrant,
  (d) a lubricant,
  (e) a plasticizer,
  (f) a colorant,
  (g) a dosing vehicle, or
  (h) any combination thereof.

27. A pharmaceutical composition comprising:
(A) insulin; and
(B) a compound having the formula

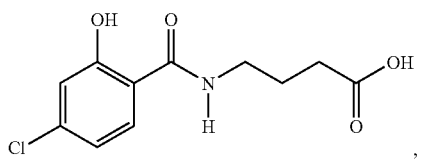

or a salt thereof.

* * * * *

UNITED STATES PATENT AND TRADEMARK OFFICE
CERTIFICATE OF CORRECTION

PATENT NO. : 7,351,741 B2 Page 1 of 1
APPLICATION NO. : 10/312703
DATED : April 1, 2008
INVENTOR(S) : John Weidner et al.

It is certified that error appears in the above-identified patent and that said Letters Patent is hereby corrected as shown below:

In the Cover page; item (75)

Please delete "Sheilds" and insert --Shields--.

Signed and Sealed this

First Day of July, 2008

JON W. DUDAS
*Director of the United States Patent and Trademark Office*